United States Patent [19]
Hutchinson et al.

[11] Patent Number: 5,912,114
[45] Date of Patent: Jun. 15, 1999

[54] WOUND DIAGNOSIS BY QUANTITATING CORTISOL IN WOUND FLUIDS

[75] Inventors: Tyrone D. Hutchinson, Irving; Hansen P. Swaniker, Arlington, both of Tex.

[73] Assignee: Johnson & Johnson Medical, Inc., Arlington, Tex.

[21] Appl. No.: 08/928,541

[22] Filed: Sep. 12, 1997

[51] Int. Cl.⁶ .......................... G01N 33/53; G01N 33/92; G01N 33/543; C12Q 1/60

[52] U.S. Cl. .................................. 435/4; 435/7.1; 435/11; 436/71; 436/131; 436/817

[58] Field of Search ................................... 435/4, 7.1, 11; 436/817, 71, 131

[56] References Cited

PUBLICATIONS

What You Need to Know About Corticosteroid Therapy, Renee L. Howser, RN, MSN,CCRN, AJN/Aug. 1995, pp. 44–49.

Human Physiology, Stuart Ira Fox, Los Angeles City College & California State at Northridge, The Endocrine System: Secretion and Actions of Hormones pp. 564–595.

*Primary Examiner*—David Saunders
*Assistant Examiner*—F. Pierre VanderVegt
*Attorney, Agent, or Firm*—Andrew C. Farmer

[57] ABSTRACT

The present invention is directed to the diagnosis and assessment of wound status by quantitating levels of cortisol present in wound fluid. The present invention is also directed to a kit and test strip for assessing wound status.

9 Claims, 5 Drawing Sheets

Wound Fluid Sample ID and Sampling Points for Subject BL

Wound Fluid Sample ID and Sampling for Subject ED

Wound Fluid Sample ID and Sampling Points for Subject EJR

Wound Fluid Sample ID and Sampling Points for Subject JY

FIG. 5A

WOUND DIAGNOSIS BY QUANTITATING CORTISOL IN WOUND FLUIDS

FIELD OF THE INVENTION

The present invention is directed to the diagnosis and assessment of wound status by quantitating levels of cortisol present in wound fluid. The present invention is also directed to a kit and test strip for assessing wound status.

BACKGROUND OF THE INVENTION

Glucocorticoids are produced and secreted by the adrenal cortex. Glucocorticoids play a key role in metabolism and immune response and are typically involved in inflammation suppression. Cortisol is a glucocorticoid found in human plasma. Approximately 95% of the body's endogenous glucocorticoid supply is cortisol. Increased amounts of cortisol are released into the blood stream when the body is subjected to physiologic stresses such as illness or trauma.

The release of cortisol is regulated by a physiologic cascade which starts at the hypothalamus. The hypothalamus produces corticotropin-releasing factor (CRF). CRF stimulates the anterior pituitary to release adrenocorticotropic hormone (ACTH). The adrenal glands are then stimulated by ACTH to secrete additional cortisol. Once the stressor-induced physiologic demands are met, the anterior pituitary is then stimulated to decrease production and release ACTH (Howser, R. L. (1995) "Corticosteroid Therapy" *American Journal of Nursing:* 44–49). Plasma cortisol levels typically vary between about 0.005 and 0.020 ng/ml normally.

It is known in the art and described for example, by Fox, S. I. (1984) "The Endocrine System, Steroid Hormones" *Human Physiology,* W. C. Brown Publishers: 564–595, that free cortisol in the blood stream is in equilibrium with cytoplasmic cortisol. However, in response to a physiologic stressor, such as trauma or disease, the cortisol equilibrium is upset and blood cortisol levels rise in response to the stressor.

Sophisticated wound diagnostics are not currently available to the wound care professional. Wound diagnosis is empirical and heavily relies on the experience and knowledge of the practitioner. Improperly diagnosed wounds such as diabetic ulcers, venous-stasis wounds and pressure sores frequently result in negative, sometimes devastating outcomes. In the past, visual wound assessments provided an indication of the approximate depth, width and discharge status of a wound. For example, venous-stasis wounds continuously discharge fluid and tend to be wide and shallow (e.g. one to two centimeters deep). Diabetic ulcers tend to be drier and deeper relative to venous-stasis ulcers. Both types of wounds are frequently found on the lower extremities of patients. Diabetic ulcers are generally found on the undersides of the feet while venous-stasis ulcers are generally found on the calves and shins. However, these wounds may also be found on the upper torso and arms. Visual wound assessments have proven to be inadequate for proper diagnosis, especially for chronic wounds. Many patients who show signs of improvement, e.g. wound-size shrinkage and discomfort reduction, subsequently develop opportunistic infection including gangrene often requiring limb amputations to save their lives.

In most cases, aggressive therapeutic intervention is not indicated after initial visual wound assessment because the practitioner is unaware of the nature and actual extent of the wound. For example, the application of a debriding agent (enzymes which destroy necrotic tissue) would be inappropriate for a chronic or exacerbated wound. Compression bandages applied to a misdiagnosed pressure sore would compromise the healing of an actual venous stasis ulcer. Fundamentally, the practitioner does not know whether a wound is likely to heal or not. Therefore, several months of trial and error therapies face a patient with a chronic, non-healing wound.

The present inventors have provided a rapid, accurate and non-invasive method to diagnose wound status in a manner which permits meaningful assessment of the wound for proper treatment and for assessing the advisability of tissue (e.g. skin) grafts. As uniquely determined by the present invention, chronic or exacerbated wounds can now be diagnosed by measuring free cortisol in wound fluid. In accordance with the present invention, it has been discovered that elevated levels of cortisol in wound fluid relative to normal plasma levels in healthy patients correlates with large, non-healing wounds. It has also been discovered herein that elevated levels of cortisol in wound fluid also correlate with inflammation and infection. Early detection of inflammation and infection in non-healing wounds permits the practitioner to begin antibiotic or anti-inflammatory regimens prior to or in conjunction with the employment advanced wound care products. Early detection of inflammation and infection in non-healing wounds also indicates the likelihood of tissue (e.g. skin) graft rejection.

Wound therapy assessment is also greatly enhanced by the present invention. In the past, the practitioner would treat a wound simply based on its outward appearance. For example, a veneous-stasis wound was conventionally treated with antibiotics, alginate dressings and/or tissue grafts. The process was hit or miss; if the prescribed treatments and/or tissue grafts were successful, then the patient was helped in the short term. But if the treatments were inappropriate, the patient could be faced with months of useless medication or additional tissue grafts, at significant cost. With the present invention, the practitioner can now quickly, more accurately and non-invasively determine the nature of a wound and prescribe an appropriate therapy for short-term remediation. The present invention provides the practitioner with crucial information about the nature and extent of the wound. Aggressive wound therapy can now be implemented or avoided depending on the wound fluid cortisol levels of a patient as determined by the present invention.

SUMMARY OF THE INVENTION

The present invention is directed to the diagnosis of wounds and specifically wound status. By wound status is meant the ability to predict whether a wound will heal in the short term (e.g. several days) or whether the wound is chronic or exacerbated and therefore non-healing. Such non-healing wounds are characterized herein as incompetent. Diagnosing wound status is meaningfully achieved for the diagnostician for the first time in accordance with the present invention rapidly (e.g. over a two to five day period), non-invasively and accurately.

In one embodiment of the present invention, wound status is determined by measuring cortisol levels in the wound. In a preferred embodiment, wound status is assessed by contacting wound fluid with an antibody reactive with cortisol, for a time and under conditions sufficient to form an antigen-antibody complex. The antigen-antibody complex, is subsequently determined and the amount of complex formed is conventionally quantitated.

In another embodiment, various consecutive wound samples are obtained so that cortisol levels are conventionally quantitated over an appropriate period, for example, from about three days to about seven days, to determine the changes in wound cortisol levels over time.

In still another embodiment, the quantity of complex formed is compared with a control blood sample from a healthy individual.

In a further embodiment, elevated wound cortisol levels compared to control or standard levels from a period of about three to about seven days, signal the practitioner to avoid attempting a tissue graft because of the increased likelihood of graft rejection.

In a preferred embodiment, the present invention is directed to a test strip or dip stick wherein an antigen-antibody/label complex is formed on the strip stick thereby providing a color reaction which correlates with levels of cortisol in the wound under diagnosis.

Still another embodiment of the present invention is directed to a compartmentalized kit which includes at least one container adapted to receive an antibody reactive with cortisol for diagnosing wound status.

A further embodiment of the present invention is directed to the diagnosis of level of inflammation and infection at a wound site by quantitating the level of cortisol present and comparing wound cortisol level with a standardized normal plasma cortisol level.

DETAILED DESCRIPTION OF THE INVENTION

The present invention provides methods for the diagnosis of wound status. In accordance with the present invention a wound is any damage leading to a break in the continuity of the skin. Wound status is the condition of a wound, examined over a course of several days to several months, which provides an indication as to whether a wound is healing or is non-healing.

A healing wound is characterized in accordance with the present invention as progressing through a normal series of stages. The healing stages include inflammation, reconstruction, epithelialization and maturation. A healing wound is also characterized in accordance with the present invention as having decreasing to normal or standard cortisol levels during the course of a several day to several week period.

Inflammation is the first biochemical response of the body to a wound. Tissue damage at the wound site triggers the complement system to release histamine from mast cells resulting in vasodilation and increased capillary permeability. The kinin system is also activated thereby attracting neutrophils to the wound site. The kinins also cause pain by stimulating sensory nerve endings.

As capillaries dilate and become more permeable, fluid flows into the injured tissue. Wound fluid contains plasma, proteins, antibodies, red and white blood cells (erythrocytes and leukocytes) and platelets.

The second stage of wound healing is reconstruction. During reconstruction macrophages produce growth factors which attract fibroblasts to the wound and stimulate the production of collagen. During reconstruction the wound starts to contract, thereby reducing the surface area of the wound. Reconstruction usually lasts about twenty-four days.

The third stage of wound healing is epithelialization. During this phase, the wound is covered by epithelial cells and scar tissue and the surface area of the wound continues to decrease. In the final stage, maturation, the scar tissue is remodeled and becomes comparable to normal tissue. The maturation stage can take up to a year or more.

In accordance with the present invention, a non-healing or incompetent wound such as, for example, a diabetic ulcer, a venous-stasis ulcer or a pressure sore is inhibited from progressing through the wound repair process and is characterized as chronically inflamed. Physiologically, a non-healing wound is characterized by the hyperactive breakdown of the Extracellular Matrix (ECM) as a consequence of elevated levels of enzymes such as metalloproteinases. Incompetent wounds are further characterized as having cortisol levels from about 30 ng/ml to about 200 ng/ml. Incompetent wounds are also characterized in accordance with the present invention as having increasing cortisol levels over a period of several days to several weeks. An incompetent wound is defined as a wound which is present for a period of several months to several years.

Wound diagnoses can accurately be determined by measuring or detecting the levels of cortisol in wound fluid. Further, wound diagnoses can be determined by correlating the level of cortisol found in a sample of wound fluid with standard or normal levels of plasma cortisol.

Measurements of cortisol in wound fluid are rapidly, accurately and non-invasively achieved for the first time with the present invention by:

(a) contacting the wound fluid with an antibody reactive with cortisol for a time and under conditions sufficient to form an antigen-antibody complex and detecting the antigen-antibody complex formed;

(b) quantitating the amount of complex obtained from step (a);

(c) repeating steps (a) and (b) to determine the change in wound cortisol levels over time; and/or (d) comparing the amount of complex obtained in step (b) with normal plasma cortisol levels, wherein an elevated level of cortisol compared to normal plasma cortisol levels correlates with an incompetent wound.

It has also been discovered in accordance with the present invention that cortisol levels correlate with wound size (see Table 1 below), inflammation and infection (see Table 2 below). In particular, elevated wound cortisol levels (relative to normal serum cortisol levels from healthy individuals) correlate with large, non-healing wounds. Wound size is measured by determining the surface area of a wound, e.g. by planimetry. Planimetry is a method for measuring the area of a plane figure by tracing its boundary line. Specifically, a photograph of a wound is taken and the boundaries of the wound are traced. The surface area of a wound, based upon its outer boundaries, is scanned into a computer and wound size is determined based on the number of pixels required to fill-in the boundary of the wound. Computer software such as SigmaScan Version 2.0 (Jandel Scientific Co., San Rafael, Calif.) and similar image measurement software conventionally available to the skilled artisan are contemplated by the present invention. Wound size can also be assessed in connection with the present invention by measuring the outer-perimeter of a wound.

Elevated wound cortisol levels also serve as an indicator of tissue graft rejection. Accordingly, and in accordance with the present invention, the practitioner can now predict the likelihood of graft failure, such as skin graft failure, based on the presence of elevated wound cortisol levels. Elevated wound cortisol levels at the site of a prospective skin graft have now been discovered to serve as a warning that a skin graft will fail unless and until cortisol levels are normalized by advanced wound care product administration, for example.

Elevated wound cortisol levels also serve as a marker for inflammation, as defined hereinabove, at the wound site. Accordingly, inflammation can be diagnosed with the present invention by:

(a) contacting wound fluid with an antibody reactive with a cortisol for a time and under conditions sufficient to form an antigen-antibody complex and detecting the antigen-antibody complex;

(b) quantitating the amount of complex obtained from step (a);

(c) comparing the amount of complex obtained in step (b) with normal plasma cortisol levels, wherein an elevated level of cortisol compared to normal plasma cortisol levels correlates with inflammation.

TABLE 1

Concentration of Cortisol in Wound Fluid and Wound Size

| Patient ID | Sampling Points | Sample ID | Cortisol Conc. ng/ml | SD | Wound Size Pixels |
|---|---|---|---|---|---|
| BL | P1 | P | 180.4 | 10.2 | 11545 |
| | P2 | M | 137.2 | 23.2 | 11545 |
| | P3 | 10 | 229.7 | 23.3 | 14080 |
| | P4 | C8 | 130.2 | 31.4 | 6717 |
| | P5 | T27 | 68.8 | 29.8 | 2571 |
| ED | P1 | C9 | 39.3 | 4.9 | 1781 |
| | P2 | T2 | 62.0 | 3.9 | 5253 |
| | P3 | T5 | 153.9 | 4.8 | 2255 |
| EJR | P1 | I | Undetected | — | 3963 |
| | P2 | F | 40.3 | 10.1 | 3981 |
| | P3 | 1X | Undetected | — | 2431 |
| | P4 | 3N | Undetected | — | 2007 |
| | P5 | C26 | Undetected | — | 2477 |
| JY | P1 | 1R | 38.8 | 2.6 | 11248 |
| | P2 | 3P | 38.1 | 1.2 | 11819 |
| | P3 | 3Q | 43.0 | 0.0 | 11819 |
| | P4 | 2P | 91.7 | n/a | 8238 |
| | P5 | 72 | 38.5 | 5.3 | 7153 |

TABLE 2

| Patient X Sample ID | Hours Fluid Serum | Cortisol Concentration ng/ml |
|---|---|---|
| 1 | 1.0 | 232.3 |
| 2 | 2.0 | 69.0 |
| 3 | 3.0 | 34.3 |
| 4 | 6.0 | 35.1 |
| 5 | 24.0 | 47.2 |
| 6 | 48.0 | 38.0 |
| 7 | 72.0 | 18.0 |

According to the present invention, wounds can be diagnosed by e.g. a simple immunoassay repeated over an effective period of time. An "effective period" of time is preferably once a month for about two to about five months. An effective period is more preferably once a day for about three to about seven days. Once levels of cortisol have been determined for a particular wound over an effective period of time, e.g. about 3 to about 7 days, the practitioner can make an accurate assessment of the appropriate modalities to employ to optimize healing and minimize treatment costs. For example, upon identification of an incompetent wound, the practitioner can, quickly begin to employ advanced wound care products to the wound site. For example, wound cortisol measurements taken over a three to five day period will provide a baseline from which the practitioner can prescribe appropriate advanced care products to patients with elevated and rising cortisol levels. Advanced wound care products may also be employed prior to establishing a baseline if wound cortisol levels are elevated relative to standard levels; the practitioner will modify the administration of wound care products, as needed, based on subsequent wound cortisol measurements. Advanced wound care products include, for example, hydrogels, compression bandages, unaboots, foam dressings, hydrocolloids, alginate dressings, debriding agents and appropriate antibiotics. Thus, once an incompetent wound has been identified, the practitioner can prescribe the appropriate therapeutic modality to hasten healing, reduce patient discomfort, and in many cases prevent limb amputations.

In conducting the present invention, wound fluid retrieval is preferably done at at least two, but preferably three different locations in each wound.

For example, wound fluid is absorbed onto filter paper. The filter paper is applied to the wound in a clockwise manner thereby absorbing wound fluid at 12, 3, 6 and 9 positions and a central location. The sampling technique is not critical, but at least two or three wound locations should be sampled because cortisol concentrations may vary at each location. However, wound fluid can also be absorbed from a single locus in a wound. The wound fluid is conventionally extracted from the filter paper and assayed by an Enzyme Linked Immunosorbent Assay (ELISA), High Performance Liquid Chromatography (HPLC), Polyacrylamide gel electrophoresis or a Radioimmunoassay, for example.

A preferred antibody is an anti-cortisol rabbit antibody (Neogen Corporation, Lexington, Ky.). Thus, the present invention provides a method for diagnosing incompetent wounds which involves contacting wound fluid from an individual to be tested for an incompetent wound with an antibody reactive with cortisol, for a time and under conditions sufficient to form an antigen-antibody complex and detecting and quantitating the antigen-antibody complex.

In another embodiment, the present invention also provides a kit for the detection of cortisol in a wound. The kit contemplated by the present invention may be used in the laboratory or hospital, for example. In general, a kit for the detection of cortisol contains at least one anti-cortisol antibody. Such an anti-cortisol antibody can be labeled with a reporter molecule or the anti-cortisol antibody can be unlabeled. The unlabeled antibody can be conventionally modified by the kit user to include a reporter molecule. The kit can be compartmentalized to include, for example, a first container of cortisol as a solution at a known concentration to act as a standard or positive control; a second container of anti-cortisol antibodies free in solution; a third container which contains a solution of secondary antibodies covalently bound to a reporter molecule which are reactive with the primary antibodies. A fourth and fifth container which contain a substrate, or reagent, appropriate for visualization of the reporter molecule.

In a preferred embodiment, the present invention is directed to a test strip or dip stick impregnated with a labeled antibody reactive with cortisol for a rapid wound diagnosis. The test strip or dip stick may be used at the bedside of a patient or in a laboratory, for example.

A test strip or dip stick of the present invention may be made, for example, from a non-porous material on which an antibody and a chromogenic substrate are coated. Upon contacting the desired wound sample with the device, the antibody/substrate and any cortisol present in the wound, interact to form a detectable color reaction on the device, for example.

In an alternative embodiment, the device may be a test strip, wherein the antibody/substrate is contained in one or more zones along the length of a strip of, e.g. fibrous material. Upon contact of one end of the strip with cortisol from wound fluid, the fluid migrates along the fibrous material. The reaction of the antibody/substrate and the production of a detectable signal indicates the presence of cortisol in the wound fluid. A color chart correlates depth of color with quantities of cortisol. For example, a very faint red color indicates cortisol at normal levels (e.g. 0.005 to 0.020 ng/ml), while a deep red color indicates cortisol at e.g. 230 ng/ml. Alternatively, the measurement region of the test strip includes several sites containing a cortisol substrate and immobilized anti-cortisol antibody. The several detection sites contain different amounts of substrate and immobilized anti-cortisol antibody, i.e., a higher amount in the first detection site and lesser amounts in subsequent sites. For example, if 20 nanograms of antibody captures the equivalent of 20 ng/min/ml of cortisol, then the first detection site of the test strip contains 40 nanograms of anti-cortisol antibody while the subsequent sites contain 60, 80, 100 and 120 etc. nanograms of antibody. Upon the addition of wound fluid, the number of sites displaying a detectable signal provides a quantitative indication of the amount of cortisol in the wound fluid sample.

The test strip or dip stick of the present invention may be any suitably absorbent, porous, chromatographic or capillary possessing material through which a test sample containing cortisol can be transported by a capillary or wicking action. The test strip may also be formulated from materials including, but not limited to: cellulose materials and nitrocellulose; fiberglass; cloth; porous gels such as silica gel, agarose, dextran and gelatin. The test strip should have an inherent strength or strength can be provided by means of a supplemental support.

The dimensions of the test strip or dip stick will be conventionally determined in accordance with, e.g. the size of the wound or the particular requirements of practitioner.

The presence of cortisol in the wound fluid of a patient can be detected utilizing antibodies conventionally available to the skilled artisan in many different types of immunoassays. A wide range of immunoassay techniques are available as can be seen by reference to Harlow, et al. (1988) *Antibodies: A Laboratory Manual*, Cold Spring Harbor Press and U.S. Pat. Nos. 4,016,043 and 4,424,279 these include ELISAs, and radioimmunoassays, for example. This, of course, includes both single-site and two-site, or "sandwich" of the non-competitive types, as well as in traditional competitive binding assays. Sandwich assays are among the most useful and commonly used assays. A number of variations of the sandwich assay technique exist, and all are intended to be encompassed by the present invention. Briefly, in a typical forward assay, an unlabeled antibody is immobilized in a solid substrate and the sample to be tested brought into contact with the bound molecule. After a suitable period of incubation, for a period of time sufficient to allow formation of an antibody-antigen binary complex, a second antibody, labeled with a reporter molecule capable of producing a detectable signal is then added and incubated, allowing time sufficient for the formation of a ternary complex of antibody-labeled antibody. Any unreacted material is washed way, and the presence of the antigen is determined by observation of a signal produced by the reporter molecule. The results may either be qualitative, by simple observation of the visible signal, or may be quantitated by comparing with a control sample containing known amounts of cortisol, for example.

Variations on the forward assay include a simultaneous assay, in which both sample and labeled antibody are added simultaneously to the bound antibody, or a reverse assay in which the labeled antibody and sample to be tested are first combined, incubated and then added to the unlabeled surface bound antibody. These techniques are well known to those skilled in the art, and the possibility of minor variations will be readily apparent. As used herein, "sandwich assay" is intended to encompass all variations on the basic two-site technique.

Cortisol may also be detected by a competitive binding assay in which a limiting amount of antibody specific for cortisol is combined with specified volumes of samples containing unknown amounts of cortisol and a solution containing a detectably labeled known amount of cortisol. Labeled and unlabeled molecules then compete for the available binding sites on the antibody. Phase separation of the free and antibody-bound molecules allows measurement of the amount of label present in each phase, thus indicating the amount of antigen in the sample being tested.

In any of the known immunoassays, for practical purposes, one of the antibodies or the antigen will be typically bound to a solid phase and a second molecule, either the second antibody in a sandwich assay, or, in a competitive assay, the known amount of antigen, will bear a detectable label or reporter molecule in order to allow visual detection of an antibody-antigen reaction. When two antibodies are employed, as in the sandwich assay, it is only necessary that one of the antibodies be specific for cortisol. The following description will relate to a discussion of a typical forward sandwich assay; however, the general techniques are to be understood as being applicable to any of the contemplated immunoassays.

In the typical forward sandwich assay, a first antibody having specificity for cortisol is either covalently or passively bound to a solid surface. The solid surface is typically a polymer, the most commonly used polymers being cellulose, polyacrylamide, nylon, polystyrene, polyvinyl chloride or polypropylene. The solid supports may be in the form of sticks, tubes, beads, discs or microplates, or any other surface suitable for conducting an immunoassay. The binding processes are well-known in the art and generally consist of cross-linking, covalently binding or physically adsorbing the molecule to the insoluble carrier. Following binding, the polymer-antibody complex is washed in preparation for the test sample. An aliquot of the sample to be tested is then added to the solid phase complex and incubated at a suitable temperature ranging from about 4° C. to about 37° C. (for example 25° C.) for a period of time sufficient to allow binding of any subunit present in the antibody. The incubation period will vary but will generally be in the range of about 1 to 40 minutes to several hours. Following the incubation period, the antibody subunit solid phase is washed and dried and incubated with a second antibody specific for the first antibody. The second antibody is linked to a reporter molecule which is used to indicate the binding of the second antibody to the first antibody. Alternatively, the first antibody may be linked to a reporter molecule which is used to indicate the binding of the first antibody to cortisol in a single step.

By "reporter molecule", as used in the present specification and claims, is meant a molecule which, by its chemical nature, provides an analytically identifiable signal which allows the detection of antigen-bound antibody. Detection may be either qualitative or quantitative. The most commonly used reporter molecules in this type of assay are either radioisotopes, enzymes, fluorophores or radionuclide containing molecules. A preferred reporter molecule is hydrazine. A most preferred reporter molecule is 2,4-dinitrophenyl hydrazine.

In the case of an enzyme immunoassay, an enzyme is conjugated to the second antibody, generally by means of glutaraldehyde or periodate. As will be readily recognized, however, a wide variety of different conjugation techniques exist, which are readily available to the skilled artisan. Commonly used enzymes include horseradish peroxidase, glucose oxidase, β-galactosidase and alkaline phosphates, among others. The substrates to be used with the specific enzymes are generally chosen for the production, upon hydrolysis by the corresponding enzyme, of a detectable color change. For example, p-nitrophenylphosphate is suitable for use with alkaline phosphatase conjugates. It is also possible to employ fluorogenic substrates, which yield a fluorescent product rather than the chromogenic substrates noted above. In one embodiment, the enzyme-labeled antibody is added to the first antibody-cortisol complex, allowed to bind, and then the excess reagent is washed away. A solution containing the appropriate substrate is then added to the ternary complex of antibody-antigen-antibody. The substrate will react with the enzyme linked to the second antibody, giving a qualitative visual signal, which may be further quantitated, e.g. spectrophotometrically, to give an indication of the amount of cortisol which was present in the sample.

Alternately, fluorescent compounds, such as fluorescein and rhodamine, may be chemically coupled to antibodies without altering their binding capacity. When activated by illumination with light of a particular wavelength, the fluorochrome-labeled antibody absorbs the light energy, inducing a state of excitability in the molecule, followed by emission of the light at a characteristic color visually detectable with a light microscope. The fluorescent labeled antibody is allowed to bind to the first antibody-cortisol complex. After washing off the unbound reagent, the remaining ternary complex is then exposed to the light of the appropriate wavelength, the fluorescence observed indicates the presence of cortisol. Immunofluorescence techniques are very well established in the art. However, other reporter molecules, such as chemiluminescent or bioluminescent molecules, may also be employed. It will be readily apparent to the skilled technician how to vary the procedure to suit the required purpose.

The following examples are intended to further illustrate the invention.

EXAMPLE 1

Wound Fluid Preparation

Wound fluid samples were collected by placing a Tegapore® prefilter over an existent venous-stasis ulcer. Samples were collected at approximately the same time each day for each patient. Sampling times are not critical, but consistent timing was employed to limit the potential effects of cortisol fluctuations as a result of the personal physiology of each patient. The prefilter inhibits, e.g. extracellular proteins, cellular debris and scar tissue from diffusing into the second Tegapore filter, thereby permitting purified wound fluid to absorb into the second filter. A preweighed Tegapore filter was placed over the Tegapore® prefilter. Wound fluid samples were quantitated by re-weighing collection filter paper, and the mass of the wound fluid was calculated by subtraction. Wound fluid samples were extracted from the filters by adding 49× the fluid mass (to give a 50:1 dilution volume:mass) of 10 mM triethanolamine (pH 7.4) with 0.1% SDS overnight at 4° C. with agitation.

Figure 1:
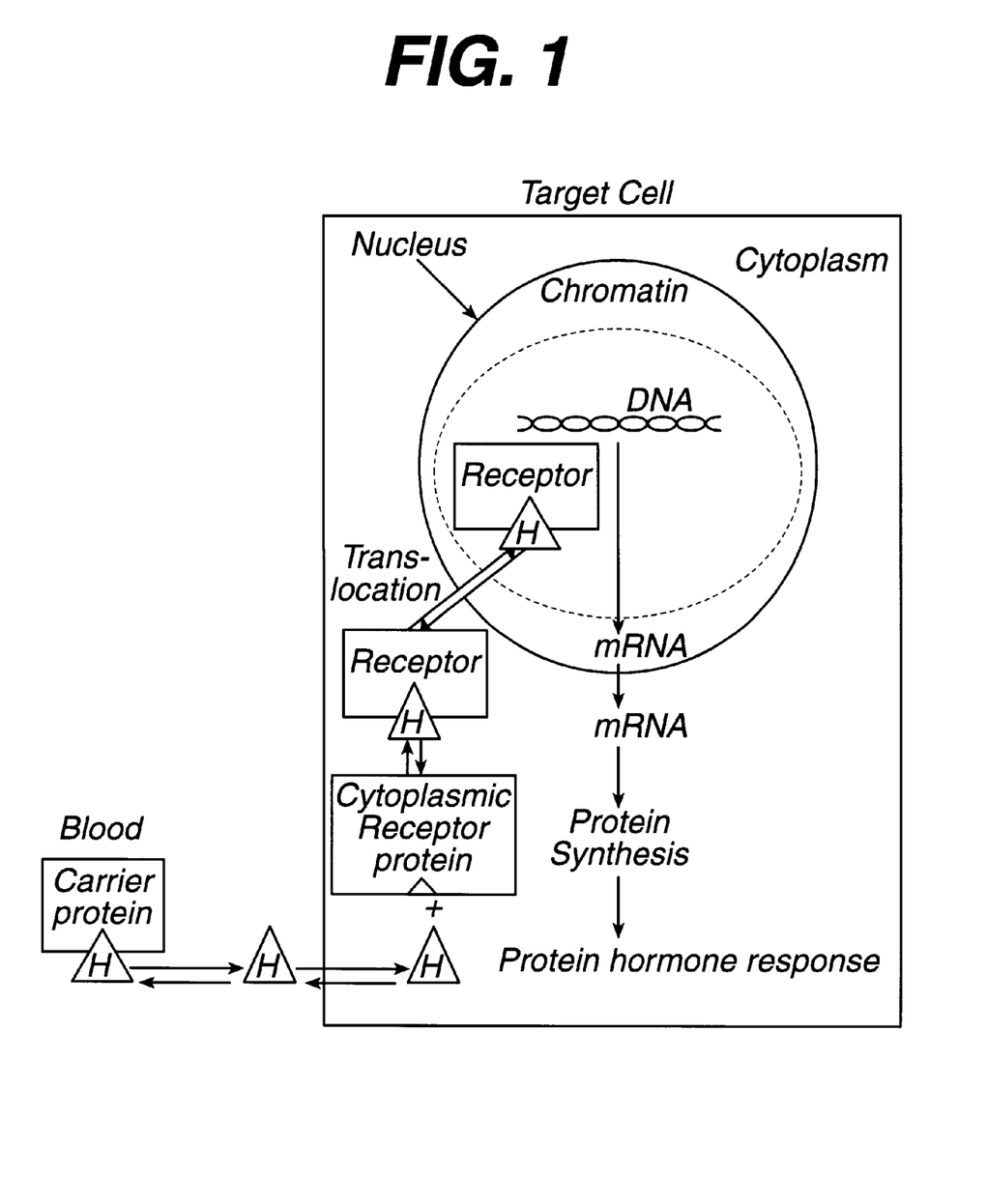
FIG. 1 illustrates the mechanism of steroid hormone (H) action on target cells.
Figure 2:
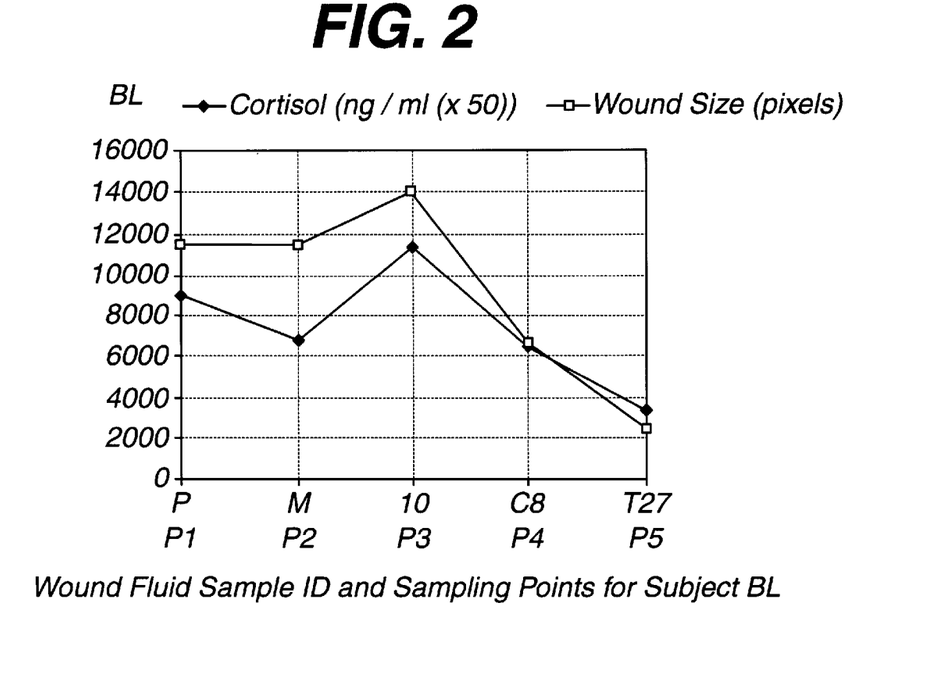
FIG. 2 is a graph showing the correlation between cortisol levels and ulcer wound size in patient BL.
Figure 2A:
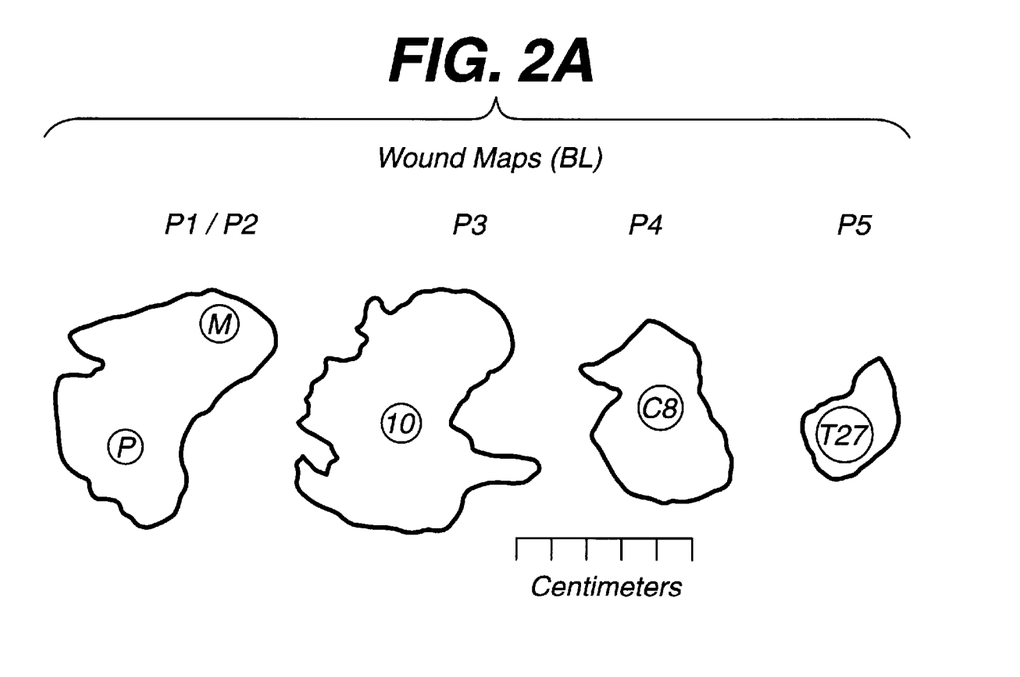
FIG. 2A is a wound map of an ulcerated wound showing (patient BL) shape, size and wound fluid sampling positions.

Patient BL presented with a veneous-stasis ulcer and exhibited an initial cortisol (same day) concentration of 180.4 ng/ml and a wound size of 11545 pixels. At P2 cortisol concentration dropped (137.2 ng/ml) while wound size remained static. The difference in cortisol concentration at P1 and P2 was due to wound sampling at two different sites in the same wound. Approximately one month elapsed between P2 and P3. At P3 cortisol concentration increased significantly (229.7 ng/ml) with concomitant wound size increase (14080 pixels). Six weeks later wound cortisol levels decreased to below P1 levels (130.2 ng/ml) and wound size also decreased (6717 pixels). Approximately six months after initial measurements, patient BL possessed a wound cortisol concentration of 68.8 ng/ml with a wound size of 2571 pixels (see FIGS. 2 and 2A). At each sampling point Patient BL was treated with the antiseptic INADINE®.

Figure 3:
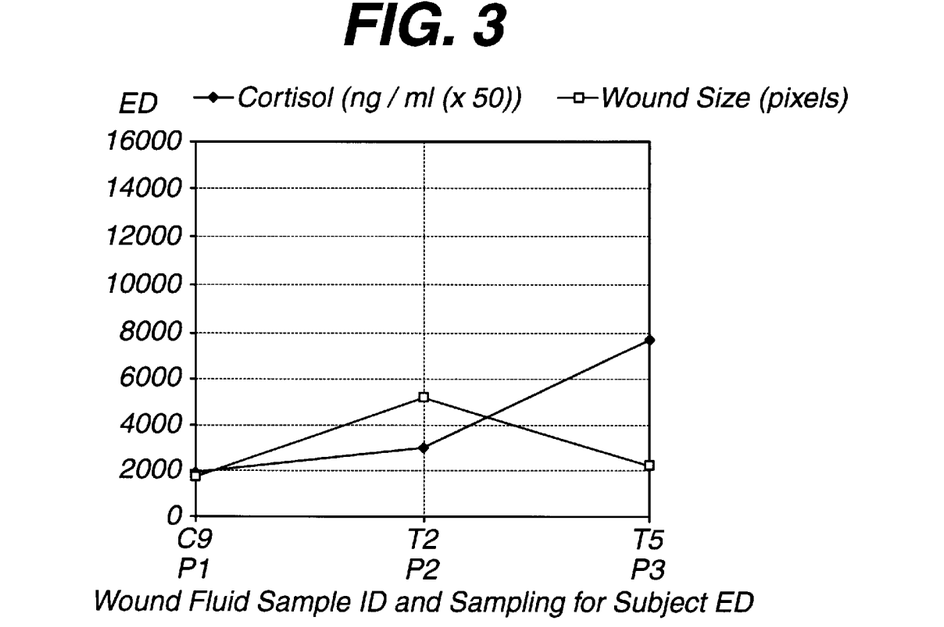
FIG. 3 is a graph showing the correlation between cortisol levels and ulcer wound size in patient ED.
Figure 3A:
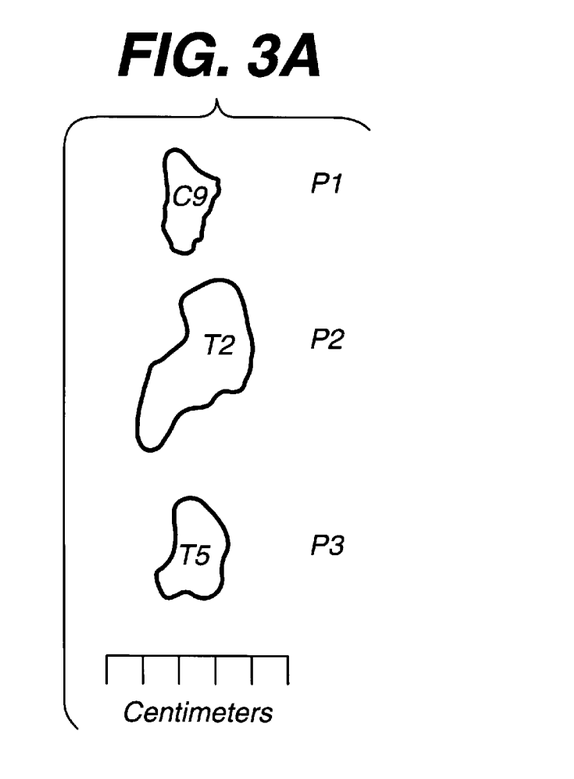
FIG. 3A is a wound map of an ulcerated wound (patient ED) showing shape, size and wound fluid sampling positions.

Patient ED presented with a leg ulcer and exhibited an initial cortisol concentration of 39.3 ng/ml with a wound size of 1781 pixels (P1). Five months later (i.e. at P2) ED possessed an increased wound fluid cortisol concentration of 62.0 ng/ml and an increased wound size 5253 pixels. One month later, ED exhibited an increased wound cortisol level 153.9 ng/ml and a decreased wound size 2255 pixels (P3). The increased cortisol levels were attributable to an insufficient wound fluid sample (see FIGS. 3 and 3A). Patient ED was initially treated with an antibiotic (FLAMAZINE®) and a TELFA® dressing at P1. At P2 an alginate gel dressing was applied to the wound with BACTEROBAN® antibiotic. FLAMAZINE® and an alginate gel dressing were applied at P3.

Figure 4:
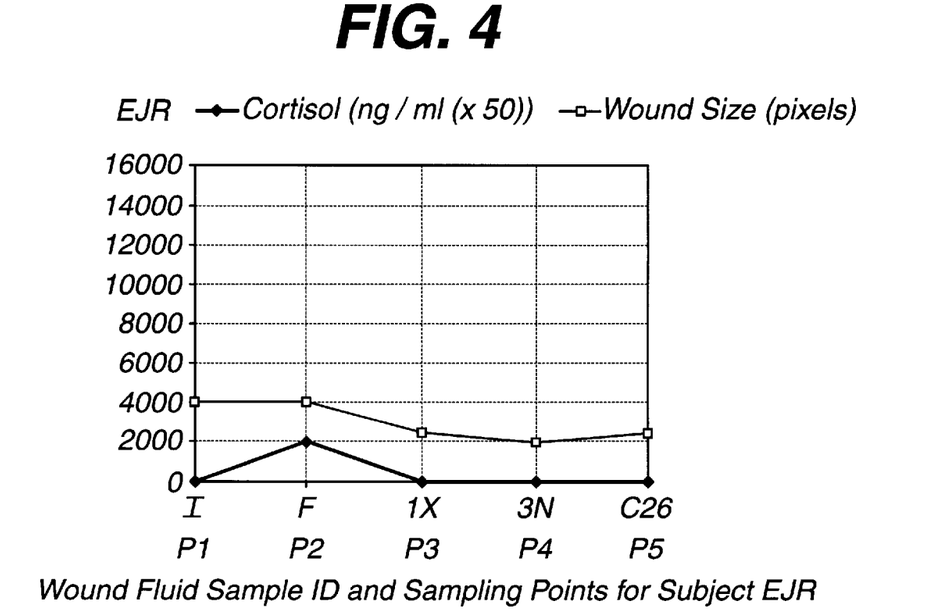
FIG. 4 is a graph showing the correlation between cortisol levels and ulcer wound size in patient EJR.
Figure 4A:
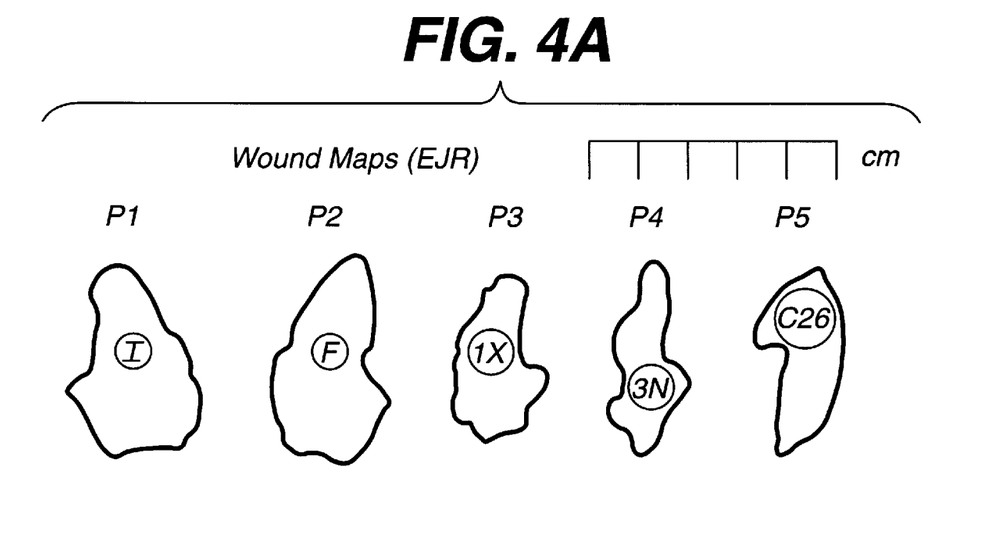
FIG. 4A is a wound map of an ulcerated wound (patient EJR) showing shape, size and wound fluid sampling positions.

Patient EJR presented with a veneous-statis ulcer but did not exhibit measurable wound fluid cortisol levels over a three month period. EJR presented with a wound size of 3963 pixels which decreased in size over the measurement period (see FIGS. 4 and 4A). EJR was treated with INADINE®, FLAMAZINE® and an alginate gel dressing.

Figure 5:
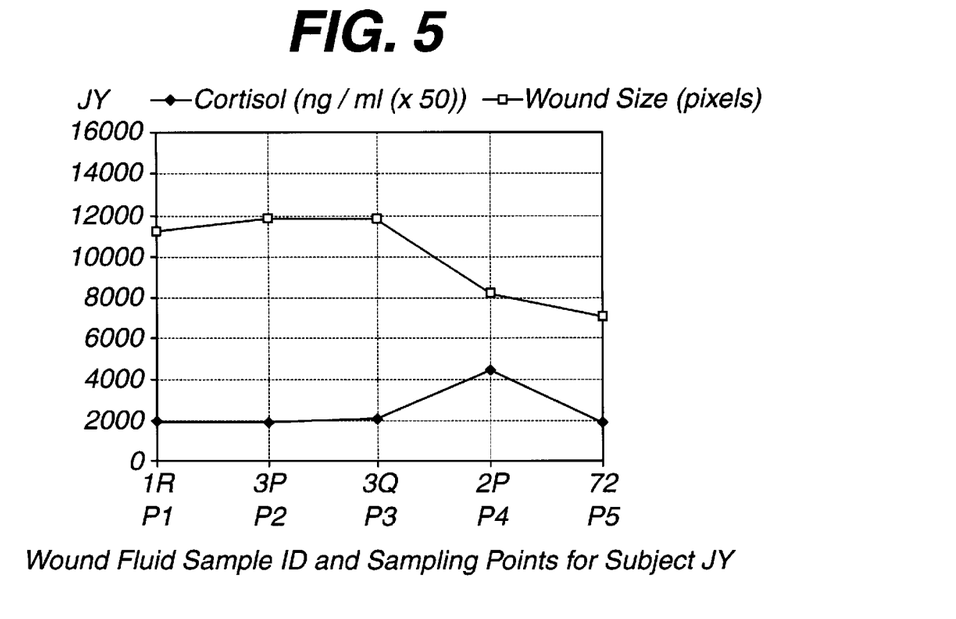
FIG. 5 is a graph showing the correlation between cortisol levels and ulcer wound size in patient JY.
Figure 5A:
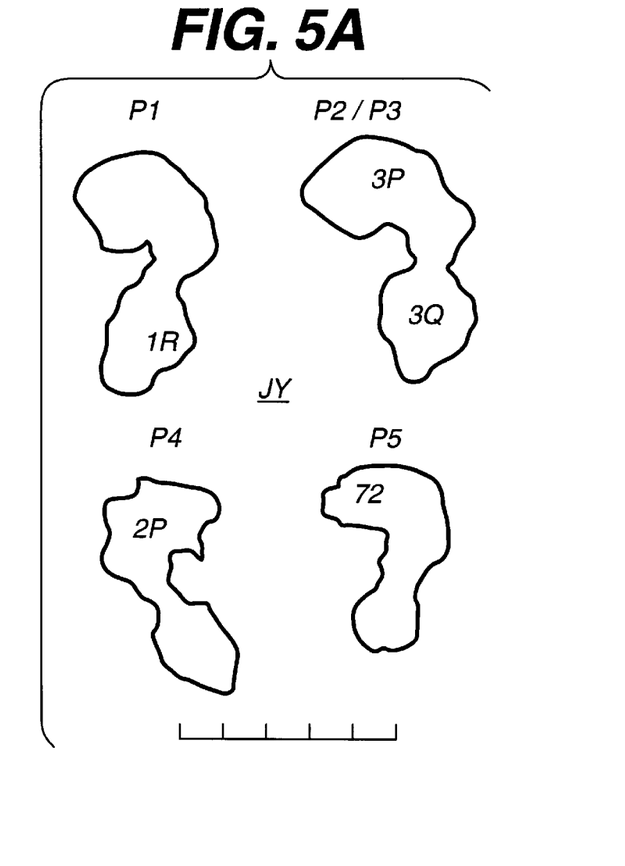
FIG. 5A is a wound map of an ulcerated wound showing shape, size and wound fluid sampling positions.

Patient JY presented with a leg ulcer and exhibited an initial cortisol concentration of 38.8 ng/ml with a wound size of 11248 pixels (PI). Less than four weeks later, JY's wound was sampled twice (P2 and P3) and possessed stable wound cortisol levels. At P4 (about two months after P1), wound cortisol levels had increased (91.7 ng/ml), yet wound size decreased. The increased cortisol levels at P4 were attributable to an insufficient wound fluid sample. At P5 wound cortisol levels had returned to baseline (PI levels) i.e. 38.5 ng/ml and wound size had decreased further to 7153 pixels. INADINE® was applied at P1–P4 while IODOFLEX® antiseptic and INADINE® were applied at P5 (see FIGS. 5 and 5A)

Patient X presented with an acute, infected leg ulcer wound and initial cortisol concentration of 232.3 ng/ml. Following treatment with an antiseptic (INADINE®) over a period of 72 hours the infection subsided and wound cortisol levels decreased to 18 ng/ml (see Table 2).

EXAMPLE 2

Measurements of wound maps were taken with SigmaScan Image Measurement Software, Version 2.0 (Jandel Scientific Co., SPSS, Inc.). Wound maps provided accurate measurements of wound size. Wound maps were scanned into a personal computer. SigmaScan Software was then used to measure the defined areas of wound map images. The "fill measurement" option provided with the software was employed to measure the area of each wound. Specifically, the area and size of each wound was determined using a pixel as the unit of measurement. The number of pixels required to fill the space within the boundary defined by a wound map determined the area and thus the size of each wound.

Patient BL's ulcer wound was measured four times during a treatment period of about eight months. Wound area increased at P3 relative to P1 and P2 but then decreased progressively at P4 and P5 (see FIG. 2A).

Patient ED's ulcer wound was measured three times during a treatment period of about four months. Wound area increased at P2 relative to P1 and then sharply decreased at P3 (see FIG. 3A).

Patient EJR's ulcer wound was measured at five time points during the three month treatment period. Wound area decreased following treatment with INADINE®, FLAMAZINE® and an alginate wound dressing (see FIG. 4A).

Patient JY's ulcer wound was measured at approximately monthly intervals during a seven month period. Between P3 and P5 wound size decreased as a result of treatment with INADINE®.

EXAMPLE 3

Cortisol Dipstick Assay

A chromogenic substrate and a reporter molecule such as 2,4-dinitrophenylhydrazine are applied to a strip of filter paper having an anti-cortisol antibody immobilized thereon and dried. The amount of substrate/reporter molecule is predetermined such that the reaction with cortisol will produce a visually detectable reaction. The tip of the paper is subsequently contacted with a wound fluid sample. If the test sample contains elevated levels of cortisol, the antibody/substrate complex reacts with cortisol and produces a detectable change in color.

What is claimed is:

1. A method for assisting the diagnosis of the status of wound healing in a patient comprising detecting cortisol levels in said wound.

2. The method of claim 1 wherein said diagnosis further comprises:

contacting wound fluid with an antibody reactive with cortisol for a time and under conditions sufficient to form an antigen-antibody complex, detecting and quantitating the antigen-antibody complex and comparing the amount of complex formed with normal plasma cortisol levels; and correlating said cortisol levels with wound status.

3. The method according to claim 2, wherein said antibody is an anti-cortisol rabbit antibody.

4. The method according to claim 2, wherein said wound is a dermal ulcer, diabetic ulcer, a venous-stasis wound or a pressure sore.

5. A method to aid in detecting the status of wound healing comprising:

(a) contacting wound fluid with an antibody reactive with a cortisol for a time and under conditions sufficient to form an antigen-antibody complex and detecting the antigen-antibody complex;

(b) quantitating the amount of complex obtained from step (a);

(c) comparing the amount of complex obtained in step (b) with normal plasma cortisol levels, wherein an elevated level of cortisol compared to normal plasma cortisol levels correlates with an incompetent wound.

6. A method for detecting cortisol levels and correlating said levels with inflammation comprising:

(a) contacting wound fluid with an antibody reactive with a cortisol for a time and under conditions sufficient to form an antigen-antibody complex and detecting the antigen-antibody complex;

(b) quantitating the amount of complex obtained from step (a);

(c) comparing the amount of complex obtained in step (b) with normal plasma cortisol levels, wherein an elevated level of cortisol compared to normal plasma cortisol levels correlates with inflammation.

7. The method of claim 2, further comprising contacting wound fluid with a test strip which comprises a support surface having disposed thereon an antibody bound to a reporter molecule operative in contact with wound fluid to develop a color indicative of cortisol.

8. A method to aid in assessing a wound comprising:

(a) contacting wound fluid from the wound with an antibody reactive with cortisol for a time and under conditions sufficient to form an antigen-antibody complex and detecting the antigen-antibody complex;

(b) quantitating the amount of complex obtained from step (a);

(c) repeating steps (a) and (b) to determine the change in wound cortisol levels over time.

9. The method according to claim 8 wherein steps a–b are repeated within about three to about seven days.

* * * * *